United States Patent [19]

Frey

[11] Patent Number: 4,704,128
[45] Date of Patent: Nov. 3, 1987

[54] ANCHORING SHANK FOR AN ENDOPROSTHESIS

[75] Inventor: Otto Frey, Winterthur, Switzerland

[73] Assignee: Sulzer Brothers Limited, Winterthur, Switzerland

[21] Appl. No.: 632,022

[22] Filed: Jul. 18, 1984

[30] Foreign Application Priority Data

Aug. 30, 1983 [DE] Fed. Rep. of Germany ....... 3331163

[51] Int. Cl.⁴ ................................................ A61F 2/32
[52] U.S. Cl. ........................................ 623/23; 623/16
[58] Field of Search ............. 128/92 C, 92 CA; 3/1.9, 3/1.91, 1.911, 1.912, 1.913

[56] References Cited

U.S. PATENT DOCUMENTS

| | | | |
|---|---|---|---|
| 4,163,292 | 8/1979 | Averett, Jr. | 623/23 |
| 4,272,855 | 6/1981 | Frey | 3/1.9 |
| 4,404,693 | 9/1983 | Zweymuller | 623/23 |
| 4,430,761 | 2/1984 | Niederer et al. | 623/23 |

FOREIGN PATENT DOCUMENTS

| | | | |
|---|---|---|---|
| 2324865 | 11/1974 | Fed. Rep. of Germany | 3/1.913 |
| 2551013 | 5/1976 | Fed. Rep. of Germany | 623/23 |
| 560042 | 3/1975 | Switzerland | 3/1.913 |
| 2069340 | 8/1981 | United Kingdom | 623/23 |

Primary Examiner—Richard J. Apley
Assistant Examiner—David Isabella
Attorney, Agent, or Firm—Kenyon & Kenyon

[57] ABSTRACT

The anchoring shank is provided in the proximal region with a rib structure formed of alternating rib crests and troughs. The troughs extend at an angle of inclination to the longitudinal axis of the shank of from 1° to 10° while the rib crests extend at a greater angle of inclination of from 2° to 12°. The troughs and rib crests, each have cross-sectional profiles which are curvilinear while the side walls of each rib are flat. In one embodiment, the radius of curvature of the troughs increase in the distal direction while the radius of curvature of the rib crests decrease in the distal direction.

13 Claims, 6 Drawing Figures

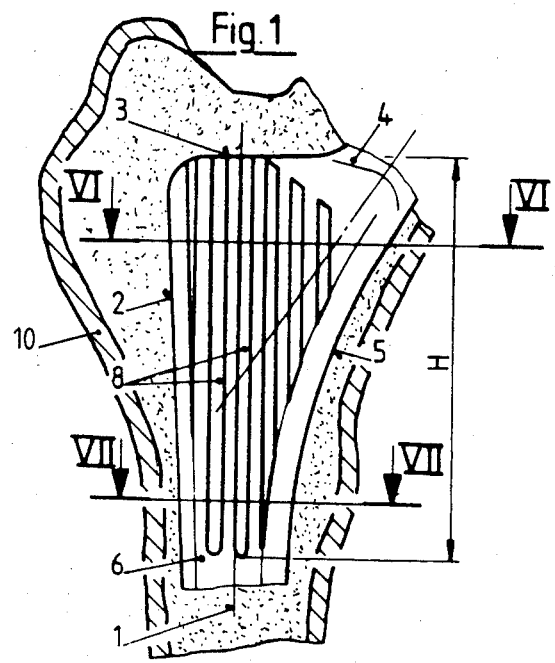
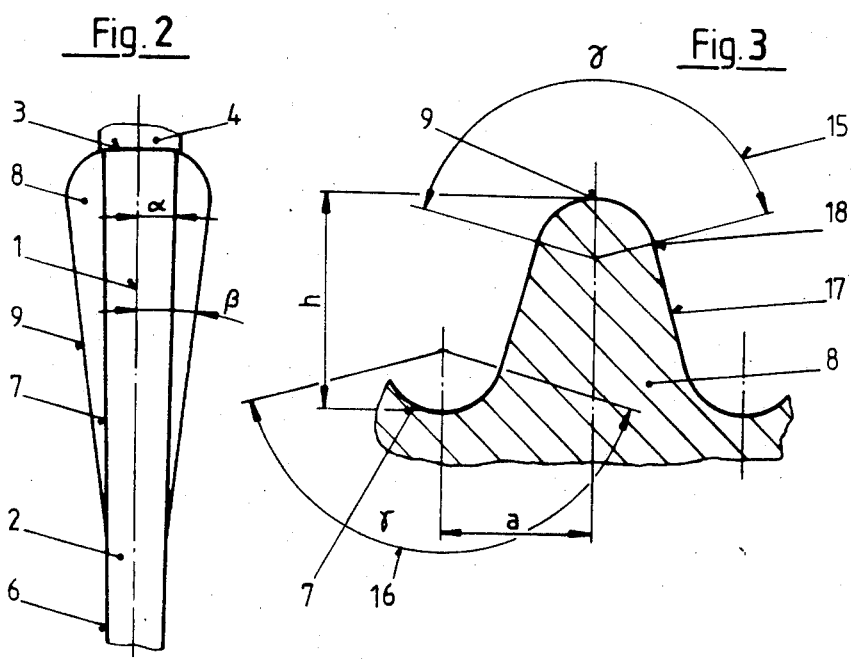

ANCHORING SHANK FOR AN ENDOPROSTHESIS

This invention relates to an anchoring shank for an endoprosthesis.

As is known, various types of anchoring shanks have been provided for endoprostheses, for example, as described in Swiss Patent No. 560,042. For example, in the case of an anchoring shank for a hip joint prosthesis, the shank has been shaped so as to receive a joint head at a point which is offset from a longitudinal axis of the shank. In such cases, in order to reduce the vertical distance, the vertical lever arm, between the "pivot" of a bending load and the point of application of the load, it has been mechanically desirable to place the anchoring which transmits the load to the bone as close as possible to the proximal end of the anchoring shank rather than to move the "pivot" and the region of the transmission of the essential forces into the lower or distal half of the shank as is otherwise customary in hip joint prosthesis.

German O.S. No. 3216539 describes a shank construction wherein the shank is provided with ribs in the proximal region; which ribs "grow" out of the shank surface at an angle. The shank is intended for cement-free anchoring and the anchoring occurs primarily in the distal shank region. In this case, in order to implant the shank, the bone is cleared out down to the cortical. The ribs which are intended to rest on the cortical also serve to prevent rotation and for secondary fixation after tissue has grown into the interstices between the ribs.

For the above noted mechanical reasons, the practice has recently been adopted to fix the anchoring shanks for a femur head prosthesis in the intertrochanteric region. When such shanks are implated without being anchored and fixed by means of a bone cement bed, one of the major problems which arises, as is known, is the primary stability of the shank in the bone, i.e. the fixation of the shank soon after implantation and before tissue has grown against the shank or, with corresponding formation of its surface such as described in U.S. Pat. No. 4,272,855, has grown into the shank surfaces. Of note, U.S. Pat. No. 4,272,855 describes the design and dimension of a surface structure for implants by which the growing in and accretion of tissue is especially supported. However, this publication gives no suggestion as to how to insure a sufficient primary stability.

As is known, one effective measure for creating primary stability consists in forming a shank, at least in the proximal or intertrochanteric region, so that the shank widens conically from the distal to the proximal in order to support and fix the shank in a compacted bed of spongious tissue. However, this conical enlargement must occur in a relatively narrow angular region. As a result, a lower limit is given, on the one hand, by the minimum compaction of the spongiosa necessary for primary stability while the upper limit of the angle of the conical expansion is determined by the fact that the radial forces exerted by the cone must not cause danger of a bursting of the cortical bone in the circumferential direction. Furthermore, at a small opening angle of the conical expansion, the conduction of the shank which occurs at the cortical edge of the resection opening is relatively slight during a driving in of the shank and is therefore insufficient.

Accordingly, it is an object of the invention to obtain a maximum compaction of spongiosa during a driving in of a prosthesis without creating a bursting effect in the cortical bone.

It is another object of the invention to facilitate the driving in of a shank at the cortical edge of a surgical opening in a bone.

It is another object of the invention to limit the amount of bone tissue to be removed for implantation of a shank of an endoprosthesis.

Briefly, the invention provides an anchoring shank for an endoprosthesis which has a longitudinal axis and a rib structure on at least one surface. The rib structure which is parallel to the longitudinal axis includes alternating rib crests and troughs. In accordance with the invention, the troughs extend at a first angle of inclination $\alpha$ to the longitudinal axis of the shank of from 1° to 10° while the rib crests extend at a second angle of inclination $\beta$ to the the longitudinal axis of from 2° to 12°. In this respect, the angle of inclination of the rib crests is greater than the angle of inclination of the troughs. Preferably, the angle of inclination of the troughs is from 2° to 5° while the angle of inclination of the rib crests is from 4° to 8°.

In addition, the rib structure is disposed in a proximal region of the shank and on two opposite side surfaces of the shank.

The shank construction allows a bone to be cleared out only to the dimensions of the shank core in the vertex region of the angle $\alpha$ so that during driving in a "base" compaction of the spongiosa or of the bone cement occurs. In this respect, the angle $\alpha$ is one-half the cone angle of the enlargement which is also the angle of inclination of the trough on the longitudinal axis of the shank. The rib crests, extending under the angle $\beta$, penetrate deeper into the spongious bone tissue or into a bone cement bed as the prosthesis is being driven in, and therefore displace and compact the tissue or bone cement more. Seen as a whole, a "mixed compaction" results which, at given angles $\alpha$ and $\beta$—which are determined essentially by the form and dimensions as well as the compaction capability of the spongiosa of an individual femur bone—results in a good primary stability without danger of bone bursting. The relatively large angle $\beta$ also allows the shank to be guided relatively early during implantation at the cortical edge of the resection opening.

The angle $\beta$ is chosen so that, except for local irregularities, the rib crests do not rest directly on the cortical of the bone, but are still embedded in spongious tissue, since—as calculations and subsequent tests have shown—the small modulus of elasticity of the spongiosa acts as shock absorption and spring support. For this reason, pronounced stress peaks do not occur on the cortical, but instead a continuous transmission of force from the shank to the bone takes place.

In the case of shanks without an edge or collar, the larger angle of inclination $\beta$ proves advantageous moreover for a "setting" of the prosthesis. Thus, in the course of time, the shank penetrates deeper into the bone, i.e. adapts to the living tissue reacting to the shank. Besides, with relatively large angles $\beta$, the "sink-in depth" can be limited. This limitation is necessary in order that the location of a joint head will not move inadmissibly far down relative to a patient's skeleton.

To avoid undercuts between the ribs and to minimize the shearing forces at the bone or at the cement bed, it is advantageous if the rib crests and troughs have an oval, circular or elliptical cross-section profile and if the rounded profile cross-section sector has an opening angle $\gamma$ of $\frac{2}{3}\pi \leq \gamma \leq \pi$. Further, undercuts can be avoided and optimum conditions for the growing in of bone tissue into the troughs between the ribs created, if the distance of two adjacent curvature centers of a trough profile and of a crest profile, parallel to the shank surface, is at least equal to the sum of the radii of curvature of the two profiles multiplied by cos $(90-\gamma/2)$, the radii of curvature being between 1 and 6 millimeters (mm). The hoped-for compaction of the spongiosa or of the cement can be increased also if the radius of curvature for the troughs increases towards the distal end and that for the crests decreases towards the distal end.

These and other objects and advantages of the invention will become more apparent from the following detailed description taken in conjunction with the accompanying drawings wherein:

FIG. 1 illustrates a schematic side view of a part of a shank constructed in accordance with the invention;

FIG. 2 illustrates a view of the shank of FIG. 1 taken from the left-hand side;

FIG. 3 illustrates an enlarged detail view of a rib crest and adjacent troughs of the rib structure in accordance with the invention taken in accordance with line VI—VI of FIG. 1;

Figure 4:
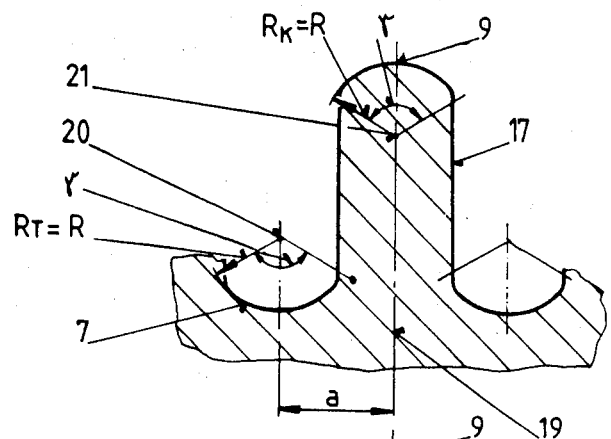
FIG. 4 illustrates an enlarged view of a rib and adjacent troughs corresponding to the line VII—VII of FIG. 1.

Referring to FIG. 1, the anchoring shank, for example, for a hip joint prosthesis has a longitudinal axis 1 which is straight for a so-called straight shank. As indicated, the shank expands conically from a distal end in symetric relation to the longitudinal axis 1 and is to be inserted into a femur bone 10 in the longitudinal direction. In addition, the shank has a lateral narrow side 2 ending in an at least nearly horizontal shoulder 3 which forms a transition to a prosthesis neck 4. The medial narrow side 5 of the shank also widens along an arc of a circle into the prosthesis neck 4 with the curved portion being disposed in the proximal shank region.

The shank has a pair of opposed blade side surfaces 6 which have surface normals which point to the anterior and posterior, respectively, when the prosthesis has been inserted. These blade sides 6 connect the narrow sides 2, 5 and are slightly open conically relative to each other from the distal end to the proximal end as indicated in FIG. 2. For example, the blade sides 6 form an opening angle $\alpha$ which is between 1° and 10°.

Referring to FIG. 1, the shank is also provided with a rib structure in the proximal region H of each blade side 6. This rib structure is formed by alternating troughs 7 and ribs 8 which have rounded rib crests 9. In addition, the troughs 7 extend at an angle of inclination $\alpha$ to the shank axis 1 of from 1° to 10° while the rib crests 9 extend at a greater angle of inclination 8 to the shank axis of from 2° to 12°. As indicated, the ribs 8 extend parallel to the longitudinal axis 1 of the shank.

Referring to FIG. 3, the troughs 7 correspond to the base level of the blade sides 6 while the vertex height h of the rib crests 9 increase from the distal end to the proximal end. The angle $\beta$ is dimensioned so that the rib crests 8 are still surrounded, at least substantially, by spongious tissue, as the spongiosa which is relatively soft as compared with the cortical, acts as shock absorption and spring support.

The rib crests 9 and troughs 7 each have a cross-sectional profile selected from one of a circular, elliptical and oval cross-sectional profile. In the simplest case, the crests 9 and troughs 7 follow the arcs of circles with radii of curvature of from 1 to 6 millimeters. Of course, any suitable continuously curved surface may be used. In addition, each rib crest 9 has a rounded profile which extends over a circular sector 15 of an angle $\gamma$ of between $\frac{2}{3}\pi$ and $\pi$. The vertex height h vertical to the blade side 6 as viewed is so great that the two sectors 15,16 of a rib crest 9 and a trough 7, respectively, are connected by way of a plane surface 17. Thus, the side walls of each rib 8 are flat. In addition, the transitions 18 between the curved and flat surfaces are "soft" in order to avoid stress peaks which may be causes of bone decomposition and fatigue breaks (fractures).

Growth of bone tissue into the shank structure can be promoted if the flat surfaces 17 extend as outwardly directed flanks of a rib 8 at most parallel to the central plane 19 as shown in FIG. 4, through a rib crest 9 or form an acute angle with the rib crest 9. This can be obtained by having the distance between two adjacent centers of curvature 20,21 of a trough 7 and an adjacent rib crest 9 parallel to the blade side or shank surface 6 made at least equal to the sum of the radii of curvature $R_K$, $R_T$ of the circles generating the profile cross-sections of the troughs 7 and rib crests 9 multiplied by the cos $(90-\gamma/2)$. For $\gamma=\pi$ and equal radii of curvature $R_K=R_T=R$ there results the simple special case: a=2 R, which, however, is not expressly illustrated.

Figure 5:
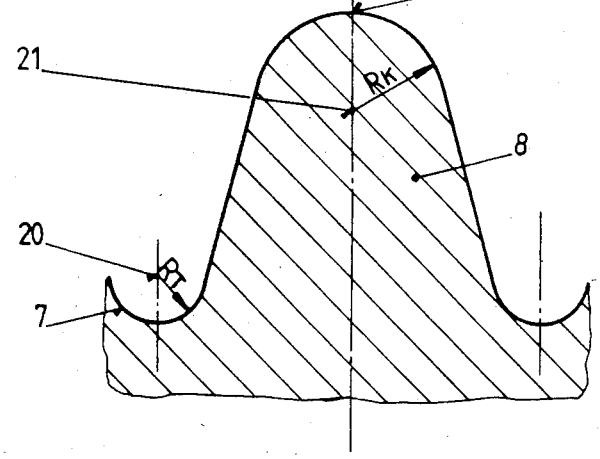
FIG. 5 illustrates a cross-sectional view of a modified rib construction in accordance with the invention.
Figure 6:
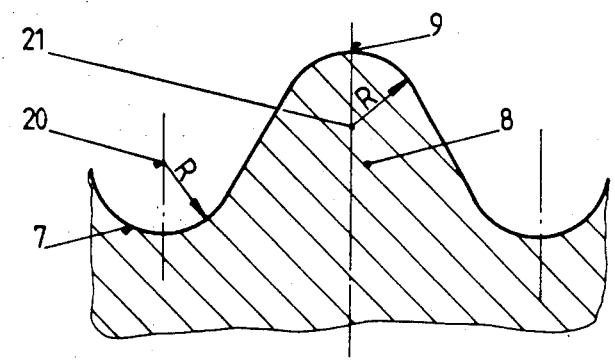
FIG. 6 illustrates a cross-sectional view taken at another point of the rib of FIG. 5.

Referring to FIGS. 5 and 6, wherein like reference characters indicate like parts as above, the rib structure may alternatively be constructed so that the troughs 7 and rib crests 9 have different radii of curvature $R_T$ and $R_K$ at the proximal ends. In addition, the relatively flat curvature with the radius of curvature $R_K$ of the rib crests 9 decreases continuously to a value $R_K=R$ in going from the proximal end to the distal end, while in the opposite direction, the trough radius of curvature $R_T$ increases steadily to the same value R.

The configuration of the shank structure with variable radii of curvature makes manufacture more expensive because of the more complicated matching than one where the troughs 7 and rib crests 9 have a constant radius of curvature throughout a profile and which can be made, e.g. with the aid of a forming cutter. However, the variable radii of curvature permits especially good compaction of the spongious bone tissue as the prosthesis is being driven in.

Of note, the rib structure is not limited to a straight shank but can be employed in like manner in conventional anchoring shanks.

The invention thus provides an anchoring shank which permits good primary stability to be obtained in the case of a cement-free anchoring while obtaining high compaction of the spongiosa and reducing the danger of the bone bursting in a circumferential direction.

Further, the invention provides a rib structure for an anchoring shank which fulfills the contradictory requirements of having large angles of inclination for high compaction and small angles of inclination to reduce the danger of bone bursting.

What is claimed is:

1. An anchoring shank for an endoprosthesis having a longitudinal axis, and a rib structure on at least one surface thereof parallel to said axis, said rib structure including alternating rib crests and troughs, said troughs extending at a first angle of inclination to said axis of from 1° to 10° and said rib crests extending at a second angle of inclination to said axis of from 2° to 12°, whereby the first angle is smaller than the second angle in any case.

2. An anchoring shank as set forth in claim 1 wherein said rib structure is disposed in a proximal region of said shank.

3. An anchoring shank as set forth in claim 1 wherein said first angle is from 2° to 5° and said second angle is from 4° to 8°.

4. An anchoring shank as set forth in claim 1 wherein said rib crests and said troughs each have a cross-sectional profile selected from one of a circular, elliptical and oval cross-sectional profile and wherein each rib crest has a rounded profile extending over a circular sector of a third angle between $\frac{2}{3}\pi$ and $\pi$.

5. An anchoring shank as set forth in claim 4 wherein the distance between two adjacent centers of curvature of a trough and an adjacent rib crest parallel to said shank surface is at least equal to the sum of the radii of curvature of said trough and said rib crest multiplied by the cosine of 90° minus one-half said third angle.

6. An anchoring shank as set forth in claim 5 wherein each said trough has an increasing radius of curvature towards a distal end of said shank and each said rib crest has a decreasing radius of curvature towards said distal end.

7. An anchoring shank for an endoprosthesis having a longitudinal axis, a pair of opposite side surfaces and a rib structure on each side surface at a proximal end thereof, each rib structure including alternating rib crests and troughs, said troughs extending at a first angle of inclination $\alpha$ to said axis of $1° \leq \alpha \leq 10°$ and each rib crest extending at a second angle of inclination $\beta$ to said axis greater than said angle of said troughs and in a range of $2° \leq \beta \leq 12°$.

8. An anchoring shank as set forth in claim 7 wherein said first angle is from 2° to 5° and said second angle is from 4° to 8°.

9. An anchoring shank as set forth in claim 7 wherein said rib crests and said troughs each have a cross-sectional profile selected from one of a circular, elliptical and oval cross-sectional profile and wherein each rib crest has a rounded profile extending over a circular sector of a third angle $\gamma$ of $\frac{2}{3}\pi \leq \gamma \leq \pi$.

10. An anchoring shank as set forth in claim 7 wherein each trough and each rib crest has a curved cross-sectional profile.

11. An anchoring shank as set forth in claim 10 wherein the distance between two adjacent centers of curvature of a trough and an adjacent rib crest parallel to a respective side surface is at least equal to the sum of the radii of curvature of said trough and said rib crest multiplied by $\cos(90-\gamma/2)$.

12. An anchoring shank as set forth in claim 10 wherein each said trough has an increasing radius of curvature towards a distal end of said shank and each said rib crest has a decreasing radius of curvature towards said distal end.

13. An anchoring shank as set forth in claim 6 wherein said axis is straight.

* * * * *

UNITED STATES PATENT AND TRADEMARK OFFICE
CERTIFICATE OF CORRECTION

PATENT NO. : 4,704,128

DATED : November 3, 1987

INVENTOR(S) : OTTO FREY

It is certified that error appears in the above-identified patent and that said Letters Patent is hereby corrected as shown below:

Column 3, line 61 change "8" to -B-

Signed and Sealed this

Nineteenth Day of April, 1988

Attest:

DONALD J. QUIGG

Attesting Officer

Commissioner of Patents and Trademarks